(12) United States Patent
Xu et al.

(10) Patent No.: US 11,446,228 B2
(45) Date of Patent: *Sep. 20, 2022

(54) NAIL COMPOSITION CONTAINING ADHESIVE AGENT, PRIMARY FILM FORMER AND PLASTICIZER

(71) Applicant: L'ORÉAL, Paris (FR)

(72) Inventors: Ruisong Xu, Scotch Plains, NJ (US); Aline Aude Guimont, Westfield, NJ (US); Allen Sha, Edison, NJ (US); Ramakrishnan Hariharan, Springfield, NJ (US); Chaitrali Makarand Gothe, Santa Clara, CA (US)

(73) Assignee: L'OREAL, Paris (FR)

( * ) Notice: Subject to any disclaimer, the term of this patent is extended or adjusted under 35 U.S.C. 154(b) by 11 days.

This patent is subject to a terminal disclaimer.

(21) Appl. No.: 16/929,745

(22) Filed: Jul. 15, 2020

(65) Prior Publication Data

US 2022/0016015 A1 Jan. 20, 2022
US 2022/0192964 A9 Jun. 23, 2022

Related U.S. Application Data

(63) Continuation of application No. 14/931,316, filed on Nov. 3, 2015, now abandoned.

(51) Int. Cl.
*A61K 8/81* (2006.01)
*A61K 8/37* (2006.01)
*A61Q 3/02* (2006.01)
*A61K 8/42* (2006.01)

(52) U.S. Cl.
CPC ............ *A61K 8/8147* (2013.01); *A61K 8/375* (2013.01); *A61K 8/42* (2013.01); *A61Q 3/02* (2013.01); *A61K 2800/26* (2013.01)

(58) Field of Classification Search
None
See application file for complete search history.

(56) References Cited

U.S. PATENT DOCUMENTS

| | | | |
|---|---|---|---|
| 5,882,636 | A | 3/1999 | Mui et al. |
| 6,630,133 | B1 | 10/2003 | Dupuis |
| 6,939,551 | B2 | 9/2005 | Amato et al. |
| 8,790,669 | B2 | 7/2014 | Li et al. |
| 2010/0278766 | A1 | 11/2010 | Ortega et al. |
| 2013/0084256 | A1 | 4/2013 | Li et al. |
| 2017/0119656 | A1* | 5/2017 | Xu .......................... A61K 8/34 |

FOREIGN PATENT DOCUMENTS

WO WO 2015/019029 2/2015

OTHER PUBLICATIONS

International Search Report dated Mar. 30, 2017, in PCT/US2016/060043.
Written Opinion of the International Searching Authority dated Mar. 30, 2017, in PCT/US2016/060043.

* cited by examiner

*Primary Examiner* — H. Sarah Park
(74) *Attorney, Agent, or Firm* — Oblon, McClelland, Maier & Neustadt, L.L.P.

(57) ABSTRACT

The present invention relates to a nail composition containing at least one adhesive agent, at least one primary film former and at least one plasticizer.

13 Claims, No Drawings

NAIL COMPOSITION CONTAINING ADHESIVE AGENT, PRIMARY FILM FORMER AND PLASTICIZER

CROSS-REFERENCE TO RELATED APPLICATIONS

The present application is based upon and claims the benefit of priority from U.S. application Ser. No. 14/931,316, filed Nov. 3, 2015, the entire contents of which are incorporated herein by reference.

FIELD OF THE INVENTION

The present invention relates to a nail composition comprising at least one adhesive agent, at least one primary film forming polymer, and at least one plasticizer.

DISCUSSION OF THE BACKGROUND

Traditional nail polish products contain a large amount of cellulose based polymers such as nitrocellulose, primarily because cellulose based polymers provide good adhesion of the compositions to nails upon application. Although nitrocellulose is the preferred adhesive agent for use in nail polish compositions and it constitutes the "gold standard" of adhesive agents in nail polish compositions, the traditional nail compositions containing nitrocellulose are generally known for poor long wear characteristics. The use of low levels of nitrocellulose tends to result in the coated films being easily damaged. On the other hand, the use of high levels of nitrocellulose results in the nail polishes being too hard and inflexible. Further, nitrocellulose does not impart high gloss.

In the past, proposed solutions to improve adhesion and gloss included incorporating into compositions containing nitrocellulose high levels of plasticizers and replacing nitrocellulose with other alternative materials. For instance, U.S. Pat. No. 6,939,551 relates to the use of nitrocellulose in the presence of butyl phthalimide isopropyl phthalimide, and U.S. Pat. No. 8,790,669 discloses the use of latex film formers instead of nitrocellulose.

Despite such attempts, there remains a need for nail compositions which adhere, are glossy and have long wear properties.

SUMMARY OF THE INVENTION

The present invention relates to a nail composition comprising:
(1) at least one adhesive agent;
(2) at least one primary film former; and
(3) at least one plasticizer.

The present invention also relates to a nail composition comprising:
(1) at least one adhesive agent;
(2) at least one primary film former; and
(3) at least one plasticizer, and
further comprising at least one co-film former, and at least one solvent. Optionally, the composition further comprises at least one secondary film former, at least one pigment, at least one thixotropic agent, at least one silicone acrylate copolymer and/or at least one additive.

The present invention further relates to the above nail compositions in the form of a base coat, a color coat or a top coat.

The present invention also relates to methods for making up and/or protecting nails comprising applying to the nails a composition of the present invention.

The present invention also relates to a method of making a nail composition comprising combining at least one adhesive agent; at least one primary film former; and at least one plasticizer in a nail composition.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Adhesion" as used herein, refers to chemical and/or physical bonding between a coating and a substrate. Good adhesion between nail polish and nail surface should translate to good wear properties on consumers.

"Adhesive agent" or "adhesive" means a polymer that improves chemical and/or physical bonding between a coating and a substrate. In this invention, the adhesive agent improves bonding between compositions and the nail surface or other compositions.

"Young's modulus" as used herein, means a force per unit area (MPa) that is needed to stretch a sample material. It is defined as the slope of stress-strain curve at the elastic region where the deformation of the sample can be restored to its original state. Stress is the force causing deformation divided by the area to which the force is applied and the strain is the deformation ratio in length to its original state. The high value of Young's modulus means that the material is hard and stiff, on the contrary low value means that the material is soft, flexible and more ductile.

"Removal" or "Easy removal" means the composition may be substantially removed with acetone or other organic solvents not limited to butyl acetate, isopropyl alcohol, ethanol, ethyl acetate, methyl acetate, methyl ethyl ketone, and mixtures thereof.

"Impact resistance" as used herein, means minimum of energy to cause failure (deformation, cracking) of the tested material. The impact energy depends on the weight used to damage a sample and the height from which the weight is dropped. Higher the weight and height from which the weight is dropped, higher is the impact energy. The impact resistance values are given in kg·cm and correspond to the lowest value of (weight×height) for which the specimen shows failure. A drop weight impact tester was used. The dynamic energy (expressed in Joule (J)) in a falling object at the impact moment can be calculated as:

$$E = F_w h = mgh, \text{ wherein}$$

$F_w$=force due to gravity—weight (N, $lb_f$)
g=acceleration of gravity (9.81 m/s², 32.17405 ft/s²)
h=falling height (m)

The equation can be combined with the equation of work:

$F=mgh/s$ s=distance

"Abrasion resistance" as used herein, means resistant to disruptions caused by being exposed to rough materials.

"Film former", "film-forming polymer" or "film forming agent" or "co-film former" as used herein means a polymer or resin that leaves a film on the substrate to which it is applied, for example, after a solvent accompanying the film former has evaporated, absorbed into and/or dissipated on the substrate.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.25% by weight, typically less than about 0.1% by weight, typically less than about 0.05% by weight, based on the total weight of the composition.

"Water free" or "free of water" herein means that water is preferably omitted (that is 0% by weight), but can be present in the composition at an amount of less than about 0.25% by weight, typically less than about 0.1% by weight, typically less than about 0.05% by weight, based on the total weight of the composition.

"Glass transition temperature" (Tg) means the temperature at which the amorphous material changes from a glassy solid state to a rubbery state. This temperature may be measured by standard techniques in the art, such as DSC (Differential Scanning calorimeter), e.g., according to the ASTM D3418-97 standard.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Making up" as used herein means to provide decoration (for example, color) to the nail. "Protecting" as used herein means to inhibit damage to the nail (for example, chipping) by providing a protective layer on the nail.

"Nails", "fingernail or "toenail" refers to a human keratinous substrate on a finger or toe which can be treated (decorated) with a single or multiple nail cosmetic compositions.

"Nail treatment system" means multiple compositions applied on the surface of nails.

"Nail composition" or "lacquer" or "nail polish" or "nail enamel" or "nail coating" or "nail film" refers to nail enamel usable as a basecoat, color coat, top coat, clear coat and protective coat applied on nails separately and/or as a combined application of the above.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Shine" or "gloss" as used herein, refers to surface shininess. Gloss meters are commonly used in the nail polish art as well as in other areas of cosmetics, and measure the amount of light reflected from the surface or film of interest. The gloss may be quantified, for example, as a % reflectance at 20°.

"Shine enhancing agent" or "shine increasing agent" in accordance with the present invention means increasing shine or, as the case may be, mitigating or reducing any reduction in shine that may result from the use of corresponding amounts of non-shine enhancing materials.

"Hardness" as used herein, means how resistant a material is to various kinds of permanent shape change when a force is applied. The force can be measured and quantified as described ahead in this application.

"Water resistance" as used herein, means resistance of a material (substance) to the penetration of water, which may cause degradation of that material. The method implemented if assessment of this invention is further disclosed "The acid number" or "the acid value" means the quantity of base, expressed in milligrams of potassium hydroxide, that is required to neutralize the acidic constituents in 1 g of sample. It allows to quantify the amount of acid present in the sample.

"Polymer or copolymer having a high acid value (number)" means polymer or copolymer which requires a high amount (in milligrams) of potassium hydroxide (KOH) to neutralize the acid that is present in one gram of a sample of the polymer (i.e., mg KOH/gram).

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Nail Composition

In accordance with the present invention, nail compositions comprising: at least one adhesive agent; at least one primary film former; and at least one plasticizer are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

In accordance with the present invention, nail compositions comprising: at least one adhesive agent; at least one primary film former; at least one co-film former; at least one plasticizer; and at least one solvent are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

According to preferred embodiments, any of the above embodiments optionally may contain at least one thixotropic agent, at least one secondary film former, at least one silicone acrylate copolymer, at least one pigment; and/or at least one additive.

In accordance with the present invention, nail compositions comprising: at least one adhesive agent; at least one primary film former; at least one co-film former; at least one plasticizer; at least one silicone acrylate copolymer and at least one solvent are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

According to these preferred embodiments, the weight ratio of at least one primary film former to the at least one silicone acrylate copolymer is greater than or equal to about 1:1, preferably between about 20:1 and about 1.5:1, preferably between about 17:1 and about 1.5:1, and preferably between about 15:1 and about 2:1, by weight, relative to the total weight of the composition, including all ranges and subranges therebetween.

According to preferred embodiments of the present invention, nail compositions (as described above) having shine (gloss) greater than about 60 GU (Gloss Units) measured at 20° angle are provided.

In accordance with the present invention, the nail compositions can be a base coat, a color coat or a top coat. However, it should be understood that each coat in the nail composition, itself, can comprise one or more layers. Thus, for example, the at least one color coat can comprise one or more color coat layers; the at least top coat can comprise one or more top coat layers; the at least one base coat can comprise one or more base coat layers. Preferably, each basecoat, color coat and topcoat compositions contain three or fewer layers of compositions, preferably two or fewer layers of compositions, and preferably a single layer of compositions.

During application of the nail composition, the base coat is typically applied directly to the nail, the color coat is typically applied either directly to the nail or to a base coat, and the top coat is typically applied to a color coat.

The nail compositions of the present invention display very strong adhesion to the nail, good wear, resistance to damage and superb gloss.

Without being bound by theory, it is believed that adhesive agent, primary film forming polymers and plasticizer present in the inventive compositions improve adhesion of the inventive nail compositions. In addition, when it is a color coat, the inventive color coat is characterized by low Young's modulus value which means that the color coat is flexible. On the other hand, when it is a top coat, Young's modulus values of the inventive top coat are higher, which is typical for hard materials. The unique combination of properties of the invention compositions deliver nail compositions which consumers can wear with minimal or no damage for an extended period (for example at least 7 to 10 days). In addition, when it is a color coat or top coat, exceptional gloss of the inventive color coat and top coat does not decrease significantly during the time of wearing.

Owing to the unique architecture of compositions of the present invention, when it is a color coat, it is characterized by shine (gloss), good flexibility and ductility (low hardness and low Young's modulus values), good water resistance and adhesion. When it is a top coat, the top coat is categorized by being relatively stiff (higher Young's modulus values), having a good water resistance and high resistance to abrasion. The top coat also has an excellent shine, which can be equal or higher than shine of the color coat.

Color Coat

According to preferred embodiments, a composition of the present invention may be a color coat.

Preferably, a color coat composition of the present invention has one or more of the following properties:

Shine (gloss) greater than about 60 GU (Gloss Units) measured at 200 angle, preferably greater than about 70 GU, preferably greater than about 75 GU;

Persoz pendulum hardness lower than about 35 oscillations, preferably lower than about 30 oscillations, preferably lower than about 25 oscillations; and Young's modulus values lower than about 45 MPa, preferably lower than about 40 MPa, preferably lower than about 35 MPa.

Preferably, a color coat composition of the present invention has a weight ratio of secondary film former to plasticizer which is greater than or equal to 1:1, by weight, relative to the total weight of the composition, preferably greater than 2:1 and preferably greater than 2.5:1.

Preferably, a color coat composition of the present invention has a weight ratio of at least one adhesive agent to at least one primary film forming polymer between about 10:1 and about 1:1, preferably between about 5:1 and about 2:1, by weight, relative to the total weight of the composition, including all ranges and subranges therebetween.

Top Coat

According to preferred embodiments, a composition of the present invention may be a top coat.

Preferably, a top coat composition of the present invention has one or more of the following properties:

Shine (gloss) greater than about 70 Gloss Units (GU) measured at 20° angle, preferably greater than 75 GU, preferably greater than 80 GU;

Young's modulus values lower than about 1200 MPa, preferably lower than about 1100 MPa, preferably lower than about 1000 MPa.

Preferably, a topcoat is clear and/or transparent. As used herein, the term "transparent" refers to that the composition has a HAZEBYK index of less than 5 as measured with a KYKHAZEGLOSS type gloss meter.

Preferably, a top coat composition of the present invention has a weight ratio of at least one primary film former to at least one plasticizer from about 0.5 to about 10, preferably from about 0.5 to about 4, by weight, relative to the total weight of the composition, including all ranges and subranges therebetween.

Adhesive Agent

In accordance with the present invention, nail compositions comprising at least one adhesive agent are provided. Preferably, the adhesive agent is chosen from the group consisting of radical or polycondensate type synthetic polymers, polymers of natural origin, and mixtures thereof.

Preferably, the adhesive agent is chosen from polysaccharide derivatives, such as cellulose or guar gum derivatives. Preferred polysaccharide derivatives include nitrocellulose or a polysaccharide ester or alkylether. The term "polysaccharide ester or alkylether" refers to a polysaccharide consisting of repeat units comprising at least two identical or different rings and having a degree of substitution per saccharide unit between 1.9 and 3, preferably between 2.2 and 2.9, and more particularly between 2.4 and 2.8. The term substitution refers to the functionalization of hydroxyl groups into ester and/or alkylether functions, and/or the functionalization of carboxyl groups into ester functions. In other words, it may consist of a polysaccharide, partially or totally substituted with ester and/or alkylether groups. Preferably, the hydroxyl groups may be substituted with $C_2$-$C_4$ ester and/or alkylether functions.

Particular mention may be made of cellulose esters (such as cellulose acetobutyrates or cellulose acetopropionates), cellulose alkylethers (such as ethylcelluloses), and ethylguars.

Preferably, the at least one adhesive agent is present in the nail compositions of the present invention at a total content greater than or equal to 0.1%, preferably from about 0.2% to about 25%, preferably from about 1% to about 20%, preferentially from about 3% to about 18%, by weight in relation to the total weight of the composition.

Plasticizers

In accordance with the present invention, nail compositions comprising at least one plasticizer are provided. Generally speaking, plasticizers are additives used to optimize the mechanical properties of films. They tend to reduce the Glass Transition Temperature (Tg) and increase the softness and flexibility of the films.

Preferably, suitable plasticizers have a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, ethyl tosylamide and mixtures thereof.

Preferably, the plasticizer is preferably present in the composition in an amount from about 0.1% to about 25% by weight, preferably from about 0.5% to about 20% by weight, preferably from about 1% to about 10% by weight, of the total weight of the composition, including all ranges and subranges there between.

Primary Film Forming Polymer

In accordance with the present invention, nail compositions comprising at least one primary film forming agent are provided. Preferred examples of primary film former agents include but are not limited to acrylic polymers (homopolymers or copolymers), preferably in the form of solid powders (flakes) and solvent free. Specific examples of suitable primary film formers include:

Synthetic polymers of the polycondensate type or of the free-radical type;

Acrylic polymers resulting from the copolymerization of monomers chosen from the esters and/or amides of acrylic acid and/or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide; and Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate.

Generally speaking, the primary film-forming polymers may be chosen from synthetic polymers such as polyurethanes, acrylic polymers, styrene acrylate copolymers, acrylate silicone copolymers, vinyl polymers, polyvinylbutyrals, alkyd resins, ketone/aldehyde resins, and resins from aldehyde condensation products, such as aryl sulfonamide formaldehyde resins such as toluene or sulfonamide formaldehyde resin.

According to particularly preferred embodiments of the invention, the primary film forming agent is selected from carboxyl functional acrylate polymers having a moderate to high glass transmission temperature (Tg) value. The "moderate to high glass transmission" as used in the context of the present invention, refers to an acrylates copolymer having Tg value ranging from about 40° C. to about 95° C., more preferably from about 60° C. to about 90° C., and more preferably from about 70° C. to about 85° C.

According to preferred embodiments, the primary film forming agent has a relatively high acid value, such as for example an acid value (number) ranging from about 40 to about 95, preferably from about 50 to about 90, and preferably from about 60 to about 80, including all ranges and subranges therebetween.

Commercially available examples of the primary film forming polymers include but are not limited to, for example, those sold under the Isocryl® name by Estron Chemicals such as, for example, Isocryl C-70 (styrene/acrylates copolymer), Isocryl N-2513, Isocryl H-60, and Isocryl H-1871.

Preferably, the primary film former(s) are present in the compositions of the present invention in amounts ranging from about 0.5% to about 20% by weight, preferably from about 1% to about 15%, and preferably from about 2% to about 10%, by weight, based on the total weight of the composition, including all ranges and subranges in between.

Secondary Film Former

According to preferred embodiments, the compositions of the present invention may also optionally include at least one secondary film forming agent chosen from epoxy resins. Suitable examples of epoxy resins include those disclosed in U.S. Pat. No. 5,001,175, the entire contents of which is hereby incorporated by reference.

Preferably, suitable epoxy resins have a glass transition temperature (Tg) of less than about 100° C., preferably less than about 80° C. Non-limiting examples of suitable epoxy resins include tosylamide epoxy resins, such as those sold by Estron Chemical under the tradename Polytex™, e.g., E-75, E-100, and NX-55, NX-3214). Other non-limiting examples of suitable epoxy resins include aryl-sulfonamide epoxy resins.

According to preferred embodiments, if present, the at least one secondary film former is present in the invention compositions in an amount ranging from about 0.1% to about 50% by weight, preferably from about 1% to about 40% by weight, and preferably from about 3% to about 15% by weight, including all ranges and subranges therebetween, all weights being based on the total weight of the composition.

Co-Film Formers

According to preferred embodiments, the compositions of the present invention may also optionally include at least one co-film forming agent. Suitable co-film forming agents include, but are not limited to, (meth)acrylate homopolymers and copolymers, polyurethanes, polyacryls, polymethacryls, cellulosic polymers, styrene-acryl copolymers, polystyrene-polyacryl mixtures, polysiloxanes, polyethers, polyesters, urethane-acryl copolymers, cellulose acetate propionate, siloxane-urethane copolymers, polyurethane-polymethacryl mixtures, silicone-acryl copolymers, vinyl acetate polymers, and mixtures thereof.

Suitable co-film forming agents also include aldehyde condensation products such as arylsulfonamide formaldehyde resins, specifically toluene sulfonamide formaldehyde resin which is a condensation product of formaldehyde and toluene sulfonamide, toluene sulfonamide/epoxy resins, e.g. tosylamide and non-drying alkyd resins, acrylic polymers and copolymers, polyurethane, polyacryls, polymethacryls, styrene-acryl copolymers, polystyrene-polyacryl mixtures, polysiloxanes, polyethers, polyesters, urethane-acryl copolymers, siloxane-urethane copolymers, polyurethane-polymethacryl mixtures, vinyl acetate polymers, and mixtures thereof.

Suitable co-film forming agents also include polyester resins formed by reacting a polyhydric alcohol with a polybasic acid, e.g., phthalic acid, such as the commercial product sold by Unitex Chemical Corporation under the name UNIPLEX 670-P, which is a polyester resin obtained by reacting trimellitic acid, neopentyl glycol, and adipic acid. (Meth)acrylic resins according to the disclosure may include copolymers of methyl methacrylate with butyl acrylate, butyl methacrylate, isobutyl methacrylate, or isobornyl methacrylate, for example, the commercial products PARALOID DM-55, PARALOID B48N, PARALOID B66, and ELVACITE 2550; copolymers of isobutylmethacrylate and butyl methacrylate, for instance, the commercial product ELVACITE 2046; and isobutyl methacrylate polymers, for example, PARALOID B67.

Suitable co-film forming agents also include polymers of natural origin, such as plant resins such as dammars, elemi, copals, benzoin; gums such as shellac, sandarac and mastic.

Specific examples of suitable co-film forming agents include, but are not limited to phthalic anhydride/glycerin/glycidyl decanoate copolymer, adipic acid/neopentyl glycol/trimellitic anhydride copolymer, tosylamide/epoxy resin, butyl acetate (and) acrylates copolymer, and hydrogenated acetophenone/oxymethylene copolymer.

Preferably, if present, the at least one co-film forming agents are added to the nail compositions of the present invention in an amount ranging from about 0.1 to 10 percent, preferably from about 0.2 to 8 percent, preferably from about 0.5 to about 5 percent by weight of the total weight of the composition, including all ranges and subranges there between.

Silicone Acrylate Copolymer

According to preferred embodiments, the compositions of the present invention may also optionally include at least one silicone acrylate copolymer.

Preferably, suitable silicone acrylate copolymers have a glass transition temperature (Tg) of greater than 20° C., preferably greater than about 25° C.

Suitable examples of silicone acrylate copolymers include silicone/(meth)acrylate copolymers, such as those described in U.S. Pat. Nos. 5,061,481, 5,219,560, 5,262,087 and US 2012/0301415, the entire contents of all of which are hereby incorporated by reference.

Suitable examples also include polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Suitable examples also include polymers comprising a backbone chosen from vinyl polymers, methacrylic polymers, and acrylic polymers, and at least one chain chosen from pendant siloxane groups. Non-limiting examples of such polymers and their synthesis are disclosed, for example, in U.S. Pat. Nos. 4,972,037, 5,061,481, 5,209,924, 5,849,275, and 6,033,650, and WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Suitable examples also include silicone/acrylate graft terpolymers, for example, the copolymers described in WO 01/32727 A1, the disclosure of which is hereby incorporated by reference.

Suitable examples also include polymers comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the disclosures of which are hereby incorporated by reference.

Suitable examples also include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Preferably, if present, the at least one silicon acrylate copolymer is present in the compositions of the present invention in an amount ranging from about 0.1 percent to about 10 percent by weight, preferably from about 0.5 percent to about 8.5 percent, and preferably from about 0.25 percent to about 5 percent by weight, including all ranges and subranges therebetween, all weights being based on the total weight of the composition.

Thixotropic Agent

According to preferred embodiments, the compositions of the present invention may also optionally include at least one thixotropic agent in an amount that is sufficient to give the composition a viscosity at rest sufficient to give it the desired texture and thixotropic behavior.

In at least one embodiment, the nature and/or amount of the at least one thixotropic agent is such that, in response to a non-chemical action, for instance, a mechanical action, prior to or simultaneously with the application of the composition to the nails, the viscosity of the composition may be reversibly lowered to a value less than or equal to 0.4 Pa·s, for example, less than or equal to 0.3 Pa·s.

The at least one thixotropic agent may be chosen, for example, from hydrophilic or organophilic clays, hydrophilic or hydrophobic fumed silicas, elastomeric organopolysiloxanes, and mixtures thereof.

Clays are silicates containing a cation that may be chosen from calcium, magnesium, aluminium, sodium, potassium, and lithium cations, and mixtures thereof. As used herein, the term "hydrophilic clay" means a clay that is capable of swelling in water; this clay swells in water and forms after hydration a colloidal dispersion.

Examples of such products include, but are not limited to, clays of the smectite family such as montmorillonites, hectorites, bentonites, beidellites, and saponites, clays of the vermiculite family, stevensite, and chlorites.

These clays may be of natural or synthetic origin.

Non-limiting examples of hydrophilic clays include smectites such as saponites, hectorites, montmorillonites, bentonites, beidellite and, in at least one embodiment, synthetic hectorites (also known as laponites), for instance, the products sold by the company Laporte under the names Laponite XLG, Laponite RD, and Laponite RDS (these products include, for example, sodium magnesium silicates and sodium lithium magnesium silicates); bentonites, for instance the product sold under the name Bentone HC by the company Rheox; magnesium aluminium silicates, which may be hydrated, for instance, the products sold by the company Vanderbilt Company under the names Veegum Ultra, Veegum HS, and Veegum DGT, and calcium silicates, such as the product in synthetic form sold by the company under the name Micro-cel C.

The organophilic clays are clays modified with chemical compounds that make the clay capable of swelling in solvent media.

The clay may be chosen, for example, from montmorillonite, bentonite, hectorite, attapulgite, sepiolite, and mixtures thereof. In one embodiment, the clay is chosen from bentonite and hectorite.

The chemical compound used to modify the organophilic clay may be chosen, for instance, from quaternary amines, tertiary amines, amine acetates, imidazolines, amine soaps, fatty sulfates, alkyl aryl sulfonates, amine oxides, and mixtures thereof.

Suitable organophilic clays include, but are not limited to, quaternium-18 bentonites such as those sold under the names Bentone 3, Bentone 38, Bentone 27 V CG, and Bentone 38V by the company Elementis, Tixogel VP by the company United Catalyst, and Claytone 34, Claytone 40, and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; and quaternium-18/benzalkonium bentonites such as those sold under the names Claytone HT and Claytone PS by the company Southern Clay.

The hydrophilic fumed silicas may be obtained by high-temperature hydrolysis of a volatile silicon compound in an oxyhydric flame, producing a finely divided silica. Hydrophilic silicas have a large number of silanol groups at their surface. Such hydrophilic silicas are sold, for example, under the names Aerosil 130®, Aerosil 200®, Aerosil 255®, Aerosil 300®, and Aerosil 380® by the company Degussa, and Cab-O-Sil HS-5®, Cab-O-Sil EH-5®, Cab-O-Sil LM-130®, Cab-O-Sil MS-55®, and Cab-O-Sil M-5® by the company Cabot.

The hydrophobic fumed silicas may be obtained by modification of the surface of the silica via a chemical reaction that generates a reduction in the number of silanol groups, these groups possibly being substituted, for example, with hydrophobic groups.

The hydrophobic groups may be chosen, for instance, from:

trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references Aerosil R812® by the company Degussa, and Cab-O-Sil TS-530® by the company Cabot, dimethylsilyloxyl or polydimethylsiloxane groups, which may be obtained by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

According to one embodiment, the at least one thixotropic agent is chosen from organophilic modified clays such as hectorite modified with benzyldimethylammonium stearate.

The thixotropic agent, if present, may be present in the composition in an amount greater than or equal to 0.05 percent by weight, for example, ranging from 0.05 percent to 15 percent by weight, or greater than or equal to 0.5 percent by weight, for example, ranging from 0.5 percent to 10 percent by weight, or ranging from 0.9 percent to 7.5 percent by weight, relative to the total weight of the composition, including all ranges and subranges therebetween.

Fillers

According to preferred embodiments, the compositions of the present invention may also optionally include at least one filler. Suitable examples of fillers include mineral or organic particles of any shape, in sheet, spherical or oblong form, regardless of the crystallographic shape (for example sheet, cubic, hexagonal, orthorhombic, etc). Mention may be made of talc, mica, kaolin, polyamide (Nylon®) (Orgasol® from Atochem), poly-β-alanine and polyethylene powders, tetrafluoroethylene polymer powders (Teflon®), lauroyllysine, starch, boron nitride, acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate.

Fillers, if present, can be present particularly at a content ranging from about 0.01% to about 10% by weight, preferably ranging from about 0.1% to about 5% by weight, most preferably from about 0.5% to about 1.5%, in relation to the total weight of the inventive compositions, including all ranges and subranges therebetween.

Coloring Agent

According to preferred embodiments, the compositions of the present invention may also optionally include at least one coloring agent. Preferably, the at least one coloring agent is chosen from the group consisting of soluble dyes, pigments, nacres and glitter.

The term "soluble dyes" should be understood to refer to organic, inorganic or organometallic compounds, soluble in the composition according to the invention and intended to color said composition.

Suitable dyes are, for example, Sudan Red, DC Red 17, DC Green 6, β-carotene, soybean oil, Sudan brown, DC Yellow 11, DC Violet 2, DC Orange 5 and Quinoline Yellow.

The term "nacres" should be understood to refer to iridescent particles of any shape, particularly produced by some mollusks in their shell or by synthetic means.

The term "pigments" should be understood to refer to inorganic or organic, white or colored particles of any shape, insoluble in the composition according to the invention and intended to color said composition.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments.

Optical brighteners or fibers optionally coated with optical brighteners may also be used.

The at least one coloring agent, if present, is preferably present in a total content greater than or equal to 0.1% by weight in relation to the total weight of the layer, ranging preferably from about 0.1 to about 5%, advantageously from about 0.2 to about 3% by weight in relation to the total weight of the composition, including all ranges and subranges therebetween.

Solvents

According to preferred embodiments, the compositions of the present invention may also optionally include at least one solvent chosen from organic and inorganic solvents. Suitable solvents may particularly be chosen from:

liquid ketones at ambient temperature such as methylethylketone, methylisobutylketone, diisobutylketone, isophorone, cyclohexanone and acetone, liquid alcohols at ambient temperature such as ethanol, isopropanol, diacetone-alcohol, 2-butoxyethanol and cyclohexanol, liquid glycols at ambient temperature such as ethyleneglycol, propyleneglycol, pentyleneglycol and glycerol, liquid propyleneglycol ethers at ambient temperature such as propyleneglycol monomethylether, propyleneglycol monomethyl ether acetate and dipropyleneglycol mono-n-butylether, short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate, liquid alkanes at ambient temperature such as decane, heptane, dodecane and cyclohexane, liquid aromatic hydrocarbons at ambient temperature such as toluene and xylene, liquid silicones at ambient temperature, and mixtures thereof.

The compositions according to the invention may also comprise so-called volatile solvents.

The term "volatile solvent" refers to a solvent capable of evaporating on contact with keratin matter, in less than one hour, at ambient temperature and at atmospheric pressure.

The volatile solvents according to the invention are preferably liquid solvents at ambient temperature, having a vapor pressure different to zero, at ambient temperature and atmospheric pressure, particularly ranging from 0.13 Pa to 40,000 Pa (from 10-3 to 300 mm Hg), particularly ranging from 1.3 Pa to 13,000 Pa (from 0.01 to 100 mm Hg), and more specifically ranging from 1.3 Pa to 1300 Pa (from 0.01 to 10 mm Hg).

On the other hand, a "non-volatile solvent" evaporates on contact with keratin matter in more than one hour, at ambient temperature and atmospheric pressure.

Preferably, the compositions of the present invention comprise a solvent chosen from acetone, ethyl acetate, propyl acetate, butyl acetate, isopropyl alcohol, and mixtures thereof.

Preferably, the total solvent content in the inventive nail compositions is above about 15%, preferably above about 20%, and preferably above about 30% by weight in relation to the total weight of the composition.

Auxiliaries/Additives

According to preferred embodiments, the compositions of the present invention may also optionally include at least one additive or auxiliary commonly used in cosmetic compositions and known to a person skilled in the art as being capable of being incorporated into said compositions. Such additives or auxiliaries may be chosen from preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, actives, proteins, ceramides, plant extracts, fibers, and the like, wetting agents and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture. These additives may be present in the color coat or top coat composition in a proportion from about 0% to about 10%, such as from about 0.01% to about 7% relative to the total weight of the composition and further such as from about 0.1% to about 5%, including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to preferred embodiments of the present invention, methods for making up and/or protecting nails comprising applying to the nails at least one nail composition of the present invention in an amount sufficient to makeup or protect the nails are provided.

According to preferred embodiments of the present invention, methods for making a nail composition comprising combining at least one adhesive agent; at least one primary film former; and at least one plasticizer in a nail composition are provided.

The following Examples are intended to be non-restrictive and explanatory only, with the scope of the invention being defined by the claims.

Example 1—Method of Preparation of Inventive Compositions

Color coat: All ingredients with the exception of colorants, dimethicone and silicone acrylate were combined together and mixed with a high-speed cutting blade for 30 minutes. Then the remaining ingredients were added. The final composition was mixed by 1400 classic shaker from Red Devil Equipment Corporation for 30 minutes or with a cutting-blade. The composition was left for at least 24 hours at room temperature (18-25° C.).

Top Coat: All ingredients were combined together and mixed for 30 minutes by 1400 classic shaker from Red Devil Equipment Corporation for 30 minutes or with a cutting-blade.

Example 2—Exemplary Invention Color Coat Compositions

Inventive color coat compositions are set forth below.

| Function | INCI name | Inventive color coat 1 (% wt)* | Inventive color coat 2 (% wt)* |
|---|---|---|---|
| wetting agent | DIMETHICONE | 0.1 | 0.1 |
| sun filter | BENZOPHENONE-1 | 0.04 | 0.04 |
| solvent | ISOPROPYL ALCOHOL | 0.35 | 0.35 |
| solvent | ETHYL ACETATE | 19.69 | 19.59 |
|  | ETHYL ACETATE | 16.91 | 16.82 |
| adhesive agent | NITROCELLULOSE | 8.89 | 8.84 |
|  | ISOPROPYL ALCOHOL | 3.81 | 3.79 |
| thickener | STEARALKONIUM HECTORITE | 0.99 | 0.98 |
| adhesive agent | NITROCELLULOSE | 1.51 | 1.51 |
|  | ISOPROPYL ALCOHOL | 0.65 | 0.65 |
| pigment | BARIUM SULFATE | 0.24 | 0.24 |
|  | RED 7 LAKE | 0.18 | 0.18 |
|  | ROSIN | 0.03 | 0.03 |
| pigment | BARIUM SULFATE | 0.38 | 0.38 |
|  | RED 6 LAKE | 0.35 | 0.35 |
|  | ROSIN | 0.05 | 0.05 |
| pigment | TITANIUM DIOXIDE | 0.36 | 0.36 |
|  | OXIDIZED POLYETHYLENE | 0.01 | 0.01 |
| sun filter | OCTOCRYLENE | 0.42 | 0.42 |
| plasticizer | ETHYL TOSYLAMIDE | 6.28 | 6.94 |
| solvent | PROPYL ACETATE | 0.75 | 0.75 |
| co-film former | ADIPIC ACID/NEOPENTYL GLYCOL/TRIMELLITIC ANHYDRIDE COPOLYMER | 0.3 | 0.3 |
| solvent | BUTYL ACETATE | 0.13 | 0.13 |
| co-film former | TOSYLAMIDE/EPOXY RESIN | 0.48 | 0.48 |
| solvent | BUTYL ACETATE | 0.16 | 0.16 |
| plasticizer | TRIBUTYL CITRATE | 0.63 | 0.63 |
| co-film former | BUTYL ACETATE | 0.12 | 0.12 |
|  | ACRYLATES COPOLYMER | 0.12 | 0.12 |
| co-film former | HYDROGENATED ACETOPHENONE/ OXYMETHYLENE COPOLYMER | 0.24 | 0.24 |
| solvent | BUTYL ACETATE | 23.51 | 23.39 |
| active | CITRIC ACID | 0.04 | 0.04 |
| primary film former | STYRENE/ACRYLATES COPOLYMER[1] | 3.05 | 2.34 |
| secondary | TOSYLAMIDE EPOXY RESIN [2] | 6.46 | 6.42 |

-continued

| Function | INCI name | Inventive color coat 1 (% wt)* | Inventive color coat 2 (% wt)* |
|---|---|---|---|
| film former | BUTYL ACETATE | 2.27 | 2.26 |
| silicone acrylate copolymer | BUTYL ACETATE ACRYLATES/DIMETHICONE COPOLYMER | 0.25 0.25 | 0.5 0.5 |

(% wt)*Overall weight of individual components present in the composition.
[1] Styrene/acrylates copolymer (Isocryl C-70) from Estron Chemical
[2] Tosylamide epoxy resin (Polytex NX-3214) from Estron Chemical

Example 3—Exemplary Invention Top Coat Compositions

Inventive top coat compositions are set forth below.

| Function | INCI name | Inventive top coat 1 (% wt)* | Inventive top coat 2 (% wt)* |
|---|---|---|---|
| colorant | VIOLET 2 | 0.00 | 0.00 |
| solvent | ETHYL ACETATE | 17.57 | 22.24 |
| solvent | ETHYL ACETATE | 17.27 | 12.61 |
| adhesive agent | NITROCELLULOSE | 8.06 | 5.88 |
| | ISOPROPYL ALCOHOL | 3.45 | 2.52 |
| adhesive agent | NITROCELLULOSE | 2.89 | 3.72 |
| solvent | ISOPROPYL ALCOHOL | 1.24 | 1.59 |
| adhesive agent | CELLULOSE ACETATE BUTYRATE | 3.36 | 3.50 |
| plasticizer | ETHYL TOSYLAMIDE | 6.74 | 8.00 |
| co-film former | PHTHALIC ANHYDRIDE/ GLYCERIN/GLYCIDYL DECANOATE COPOLYMER | 0.64 | 0.70 |
| | ETHYL ACETATE | 0.27 | 0.30 |
| solvent | BUTYL ACETATE | 36.70 | 36.94 |
| primary film former | STYRENE/ACRYLATES COPOLYMER[1] | 0.91 | 1.00 |
| silicone acrylate copolymer | ACRYLATES/DIMETHICONE COPOLYMER | 0.46 | 0.50 |
| | BUTYL ACETATE | 0.46 | 0.50 |

(% wt)*Overall weight of individual components present in the composition.
[1] Styrene/acrylates copolymer (Isocryl C-70) from Estron Chemical

Example 4—Comparative Compositions

As discussed below, inventive compositions were compared for various properties against the following comparator formulations:

Comparator A

Color coat: butyl acetate, ethyl acetate, nitrocellulose, acetyl tributyl citrate, isopropyl alcohol, adipic acid/neopentyl glycol/trimellitic anhydride copolymer, glycidoxypropyl polysilsesquioxane, stearalkonium bentonite, n-butyl alcohol, styrene/acrylates copolymer, titanium dioxide, barium sulfate, colophonium (rosin) (colophane), silica, benzophenone-1, pigment.

Top coat: ethyl acetate, butyl acetate, cellulose acetate butyrate, isopropyl alcohol, acetyl butyl citrate, glycidoxypropyl popysilsesquioxane, bis-hemapoly(1,4-butanediol)-22?IPDI copolymer, acrylates copolymer, adipic acid/neopentyl glycol/trimellitic anhydride copolymer, trimethylpentanediyl dibenzoate, acetone, bis-trimethylbenzoyl phenylphosphine oxide, benzophenone-3, pigment.

Comparator B

Color Coat: butyl acetate, ethyl acetate, nitrocellulose, acetyl tributyl citrate, isopropyl alcohol, tosylamide/epoxy resin, stearalkonium bentonite, triphenyl phosphate, glycidyl neodecanoate/phthalic anhydride/tmp crosspolymer, aqua/water/eau, adipic acid/neopentyl glycol/trimellitic anhydride copolymer, calcium aluminum borosilicate, calcium sodium borosilicate, synthetic fluorphlogopite, isosorbide dicaprylate/caprate, silica, diacetone alcohol, etocrylene, kaolin, hydroxyethyl acrylate/ipdi/ppg-15 glyceryl ether copolymer, acrylates/dimethicone copolymer, *corallina officinalis* extract, tocopheryl acetate, phosphoric acid, trimethylsiloxysilicate, dimethicone, cetyl peg/ppg-10/1 dimethicone, styrene/acrylates copolymer, polyvinyl butyral, carthamus tinctorius (safflower) seed oil, butylene glycol, macrocystis pyrifera (kelp) extract, hydrolyzed conchiolin protein, methylparaben, propylparaben, colorants.

Topcoat: ethyl acetate, butyl acetate, isopropyl alcohol, cellulose acetate butyrate, mek, adipic acid/neopentyl glycol/trimellitic anhydride copolymer, acetyl tributyl citrate, sucrose benzoate, n-butyl alcohol, ethyl trimethylbenzoyl phenylphosphinate, etocrylene, hydroxyethyl acrylate/ipdi/ppg-15 glyceryl ether copolymer, water, diamond powder, alumina, methyltriethoxysilane, platinum powder, silica, colorants.

Comparator C

Color Coat: ethyl acetate, butyl acetate, propyl acetate, nitrocellulose, tosylamide epoxy resin, isopropyl alcohol, acetyl tributyl citrate, ethyl tosylamide, acrylates copolymer, stearalkonium hectorite, tributyl citrate, octocrylene, titanium dioxide, adipic acid/neopentyl glycol/trimellitic anhydride copolymer, hydrogenated acetophenone/oxymethylene copolymer, rosin, oxidized polyethylene, dimethicone, citric acid, benzophenone-1, colorants.

Topcoat: butyl acetate, ethyl acetate, nitrocellulose, ethyl tosylamide, isopropyl alcohol, cellulose acetate butyrate, acrylates copolymer, acetyl tributyl citrate, adipic acid/ neopentyl glycol/trimellitic anhydride copolymer, violet 2.

Example 5—Evaluation of Inventive Compositions: Methods

Sample Preparation for In Vitro Testing:

In order to prepare samples of the inventive compositions and comparators compositions for in vitro tests, 6 mil of a tested product was applied on a substrate specific for a test by using a drawdown bar with a microprocessor controlled film applicator (Coatmaster 509 MC from Erichsen) at a speed of 25 mm/s. The samples were dried for 24 hours at room temperature.

In vitro shine (gloss) evaluation: A thin layer of a tested composition was applied on a drawdown chart (Bykoopacity chart 5C, 7.6×10.25 inch) according to the method described above. Gloss of the coating was measured at 20° by using the Micro-TRI-Gloss meter, available from BYK-Gardner and expressed by gloss units (GU).

In vitro hardness evaluation: A thin layer of a tested composition was applied on a glass plate (customer-made, 4×6 inch) by using the same method as described above. The hardness of the coatings was measured by Pendulum Hardness Tester (Persoz pendulum) equipped with a temperature and humidity control chamber (30±2° C., 70±2% RH) according to ASTM method D4366-95. In order to determine the hardness, number of oscillations of the pendulum during 1 minute was counted. Low number of oscillations (0-50 oscillations per minute) characterized soft material, while high number (>50 oscillations per minute) was typical for hard materials.

In vitro adhesion evaluation: A layer of the tested compositions were applied on Vitro-nails substrate from IMS test group according to the method described above. Adhesion properties were quantified by in-vitro method Reference #ISO/DIN 2409, ASTM D3359. The adhesion properties were visually evaluated according to the scale below:

| Classification | Percent area removed |
| --- | --- |
| 5 | 0%-None |
| 4 | Less than 5% |
| 3 | 5-15% |
| 2 | 15-35% |
| 1 | 35-65% |
| 0 | Greater than 65% |

In vitro soapy water evaluation: The tested compositions were applied on plastic nail spoons from Daret Inc. Each nail spoon was treated with two coats of the tested composition, each coat was applied by a nail brush (the second coat was applied two minutes after the first coat) and then dried at room temperature for 24 hours. Then the spoons were immersed in a soapy water batch (1.4 g of Redken superbrew shampoo and 1 g of hand soap in 225 mL water) at 45° C. for 20 minutes and dried out with a cotton tissue. The dry samples were visually inspected for shine and color change, then abraded with a metal object (quarter) and again visually inspected for shine loss and/or color change on the surface. The scuffing was performed also for samples which were not exposed to the soapy water. All, samples were graded according to the following scale: "poor"-significant shine and color loss in comparison to the control sample (unscratched sample), "fair"—slight shine and color loss and "good"—almost no change in shine and color loss.

In vitro Young's modulus evaluation: A layer of tested product was applied according to the procedure already described on polypropylene (PP) substrate. The samples dried at room temperature (20-25° C.) for 4 to 7 days. Then, the film was removed from the substrate and cut by DMA film cutter from TA instrument (5.3 mm cutter, PN 984485.901 and Young's modulus was measured by using a Dynamic Mechanic Analyzer (Q800 from TA instruments) at 30° C. The hardness was expressed by Modulus values (MPa). Low number of MPa (0-100) characterized soft materials, while higher number (100-400) was typical for hard materials and very high number of MPa (>400) was specific for a very hard materials.

In vitro abrasion resistance: The abrasion resistance was tested on a BYK-Gardner™ 'Scrub' Abrasion Tester Model AG-8100. Each of the tested compositions was applied on a black Byko Charts scrub test panel by depositing the product as described above. The samples dried at room temperature (20-25° C.) for five days. Then the samples were scrubbed by a nylon brush (from BYK) with one kg load for 2×300 cycles with 30 cycles per minute. After the first 300 cycles, the brush was turned off. The gloss was measured before and after scrubbing using Micro-TRI-Gloss meter, available from BYK-Gardner, Columbia, Md. The reading at 60° degree was used for comparison. Following an arbitrary reading, it was determined that if the gloss damage was less than 10%, the abrasion resistance was defined as high, 10-20% as medium, and more than 20% as low.

Example 6—Evaluation of Inventive Compositions: Results

TABLE 3

Comparative studies of Inventive Compositions vs. Comparators A, B and C are set forth below:
Comparison of color coat compositions*:

| | Shine at 20° | Persoz pendulum Hardness | Water resistance | Adhesion to Vitro Nails | Young's Modulus (MPa) |
| --- | --- | --- | --- | --- | --- |
| Comparator A | 50.3 | Low (49) | Fair | Good | Low (39) |
| Comparator B | 51.5 | High (75) | Fair | Good | High (148) |
| Comparator C | 67 | Low (39) | Good | Good | Low (34) |
| Inventive 1 | 70.9 | Low (32) | Good | Good | Low (44) |
| Inventive 2 | 68.9 | Low (30) | Good | Good | Very Low (33) |

*Experiments for particular samples were conducted on the same day, however, the specific parameters were tested on different days. Shine and hardness were measured at different days under defined experimental conditions.

As per the results shown above, the inventive compositions had superior gloss comparing to tested comparators. The adhesion measurements of inventive 1 and 2 were at parity with the comparative compostions, while water resistance was better for inventive compositions than for comparator A and B and was at parity with comparator C. The measurements of hardness and Young's modulus for the inventive compostions were at parity with comparator A and C and lower than comparator B which indicates good wear of inventive compostions 1 and 2.

TABLE 4

Comparison of top coat compositions*:

| | Shine at 20° | Persoza Pendulum Hardness | Water resistance | Young's Modulus (MPa) | Abrasion resistance |
| --- | --- | --- | --- | --- | --- |
| Comparator A | 69.1 | 185 | Good | 874 | Medium |
| Comparator B | 60.6 | 211 | Good | 1601 | Medium |
| Comparator C | 76.4 | 90 | Good | 438 | Medium |
| Inventive 3 | 80.2 | n/a | Good | 1161 | High |
| Inventive 4 | 81.4 | n/a | Good | 482 | High |

*Experiments for particular samples were conducted on the same day, however, the specific parameters were tested on different days. Shine and Young's modulus were measured at different days under defined experimental conditions. The presented data were collected on different days.

The preceding table lists the in vitro performance comparison of the inventive top coats compositions and comparators. As per the results, the inventive compositions had higher gloss values than the comparative compostions. The water resistance of the inventive compostions was at parity with the comparators and the abrasion resistance was higher. In addition, Young's modulus measurements were the highest for comparator B, followed by inventive composition 3, comparator A, inventive composition 4 and comparator C. Those results show that the inventive composition 3 was harder than inventive composition 4 and comparators A and C but less hard than comparator C. These parameters indicate good resistance to damage of inventive compostions.

Example 7—Plasticizers and Film Former Selection

In order to select the most suitable plasticizer for inventive compositions, various plasticizers were evaluated for shine according to the described method. The different plasticizers were incorporated into a base composition (Base) containing nitrocellulose (28%), isopropyl alcohol (12%) and butyl acetate (60%).

In order to evaluate primary film formers, six different compounds were incorporated into a base composition (Base) and were evaluated for shine, hardness, adhesion and Young's modulus. Based on the above presented measurements, compositions containing tosylamide/epoxy resin were characterized to have the highest value of shine,

TABLE 5

Selection of plasticizers*

| | Exp 1* | Exp 2* | Exp 3* | Exp 4* | Exp 5* | Exp 6* | Exp 7* | Exp 8* | Exp 9* |
|---|---|---|---|---|---|---|---|---|---|
| Base (42.86% in all exp.) | Yes | Yes | Yes | Yes | Yes | Yes | Yes | Yes | Yes |
| Ethyl tosylamide | 2% | 5% | 8% | — | — | — | — | — | — |
| sucrose acetate isobutyrate | — | — | — | 2.22% | 5.56% | 8.90% | — | — | — |
| acetyl tributyl citrate | — | — | — | — | — | — | 2% | 5% | 8% |
| Butyl acetate (QS in all exp) | 55.14% | 52.14% | 49.14% | 54.92% | 51.58% | 48.25% | 55.14% | 52.14% | 49.14% |
| Shine @ 20° | 73.9 | 7707 | 81.4 | 67 | 65.5 | 70.1 | 69.1 | 69.9 | 70.4 |

*Experiments for presented examples were conducted on different days.

Based on the results provided above, ethyl tosylamide had the highest value of shine. It was followed by sucrose acetate isobutyrate and acetyl tributyl citrate.

TABLE 6

Selection of primary film formers*

| | Exp 1 | Exp 2 | Exp 3 | Exp 4 | Exp 5 | Exp 6 | Exp 7 |
|---|---|---|---|---|---|---|---|
| Base (as described above) | Yes | Yes | Yes | Yes | Yes | Yes | Yes |
| ethyl tosylamide | 5.00% | 5.00% | 5.00% | 5.00% | 5.00% | 5.00% | 5.00% |
| butyl acetate (and) acrylates copolymer | — | 6.67% | — | — | — | — | — |
| adipic acid/neopentyl glycol/trimellitic anhydride copolymer | — | — | 4.76% | — | — | — | — |
| tosylamide/epoxy resin | — | — | — | 4.44% | — | — | — |
| styrene/acrylates copolymer* | — | — | — | — | 6.67% | — | — |
| phthalic anhydride/glycerin/glycidyl decanoate copolymer | — | — | — | — | — | 4.76% | — |
| tosylamide epoxy resin (and) butyl acetate** | — | — | — | — | — | — | 4.44% |
| Butyl acetate (QS) | 52.14 | 45.47 | 47.38 | 47.70 | 45.47 | 47.38 | 47.70 |
| Shine @ 20° | 76.6 | 72.5 | 78.2 | 79.8 | 77.5 | 79.2 | 79.2 |
| Hardness | 281 | 294 | 238 | 243 | 278 | 274 | 250 |
| Adhesion | 2 | 0 | 0 | 1.75 | 2 | 1.75 | 3 |
| Young's Modulus (MPa) | 1732 | 987 | 121 | 984 | 1717 | 1724 | 940 |

*Experiments for each of the presented examples were conducted on different days.
ISOCRYL C-70- STYRENE/ACRYLATES COPOLYMER*POLYTEX NX-3214- TOSYLAMIDE EPOXY RESIN (74%) (and) BUTYL ACETATE (26%)

followed by phthalic anhydride/glycerin/glycidyl decanoate copolymer and tosylamide epoxy resin (and) butyl acetate, both generating the same shine.

As per results presented above, compositions containing styrene/acrylates copolymer, phthalic anhydride/glycerin/glycidyl decanoate copolymer and tosylamide epoxy resin (and) butyl acetate (epoxy resin) demonstrated better adhesion property than their counterparts. However, addition of adipic acid/neopentyl glycol/trimellitic anhydride copolymer enhanced the film with more flexibility than other film formers which illustrates that it can be a good plasticizer.

What is claimed is:

1. A nail composition comprising:
   at least one adhesive agent, wherein the at least one adhesive agent is nitrocellulose;
   at least one primary film former, wherein the at least one primary film former is a carboxyl functional acrylate;
   at least one secondary film former;
   at least one co-film former selected from the group consisting of polyurethanes, acrylic polymers, vinyl polymers, polyvinylbutyrals, and mixtures thereof; and
   at least one plasticizer;
   wherein the composition has shine higher than about 60 GU at 20°.

2. The nail composition of claim 1, further comprising at least one solvent.

3. The nail composition of claim 1, wherein the weight ratio of at least one primary film former to at least one plasticizer is greater than or equal to about 1:1.

4. The nail composition of claim 1, wherein the at least one primary film former is a carboxyl functional acrylate polymer having an acid value (number) ranging from about 40 to about 95.

5. The nail composition of claim 1, wherein the at least one primary film former has a Tg value ranging from about 40° C. to about 95° C.

6. The nail composition of claim 1, wherein the at least one secondary film former is tosylamide epoxy resin.

7. The nail composition of claim 1, wherein the at least one plasticizer is selected from the group consisting of glycols and their ester derivatives, esters of acids carboxylic acids, and mixtures thereof.

8. The nail composition of claim 1, wherein the at least one co-film former is selected from the group consisting of acrylic polymers, vinyl polymers, polyvinylbutyrals, and mixtures thereof.

9. The nail composition of claim 2, wherein the at least one solvent is selected from organic solvents, inorganic solvents, and mixtures thereof.

10. The nail composition of claim 1, wherein the composition is a color coat, topcoat or basecoat.

11. The nail composition of claim 1, further comprising at least one coloring agent.

12. A method of making up or protecting nails comprising applying the composition of claim 1 to nails in an amount sufficient to make up or protect the nails.

13. A method of making the composition of claim 1, comprising combining the at least one adhesive agent, at least one primary film former, and at least one plasticizer in a nail composition.

* * * * *